United States Patent [19]

Bentley et al.

[11] 4,164,221

[45] Aug. 14, 1979

[54] ATRAUMATIC BLOOD ACCESS DEVICE VALVE

[75] Inventors: Donald J. Bentley, Newport Beach; Donald A. Raible, Orange, both of Calif.

[73] Assignee: Bentley Laboratories, Inc., Irvine, Calif.

[21] Appl. No.: 813,527

[22] Filed: Jul. 28, 1977

[51] Int. Cl.² ............................................. A61M 5/00
[52] U.S. Cl. ................................ 128/214 R; 128/274; 128/348; 251/291; 251/319
[58] Field of Search .................... 128/214 R, 274, 348, 128/350 R, 1 R; 137/319, 322; 251/145, 291, 318, 319

[56] References Cited

U.S. PATENT DOCUMENTS

| | | | |
|---|---|---|---|
| 1,483,964 | 2/1924 | Abramovitz | 137/319 |
| 2,298,632 | 10/1942 | Thorner | 251/319 |
| 3,765,032 | 10/1973 | Palma | 128/214 R X |
| 3,826,257 | 7/1974 | Buselmeier | 128/214 R |
| 3,991,756 | 11/1976 | Synder | 128/214 R |
| 4,015,601 | 4/1977 | Bokros et al. | 128/214 R |
| 4,108,173 | 8/1978 | Slivenko et al. | 128/214 R |
| 4,108,174 | 8/1978 | Slivenko | 128/214 R |

Primary Examiner—Dalton L. Truluck
Attorney, Agent, or Firm—Lyon & Lyon

[57] ABSTRACT

An atraumatic valving mechanism and its method of operation for use within the blood passageway of a blood access device, the blood passageway connecting a blood vessel within the body to the body exterior. The valving device includes a plugging means for effecting a seal within the blood passageway and for substantially expelling the blood from the device upon closing, and a reciprocal stem which is connected to the plugging means and may be pushed or pulled in order to close or open the blood access device valve as desired. The valving mechanism includes a disposable connectable valve chamber which is adapted to be secured about that portion of the blood access device blood passageway located at the body exterior. The connectable valve chamber includes a blood outlet for blood flow in communication with the body blood vessel through the blood access device blood passageway and valve chamber and an aperture through which the reciprocal stem may be alternately actuated in order to open and close the device in a sterile manner without trauma to the body or blood passing therethrough.

6 Claims, 6 Drawing Figures

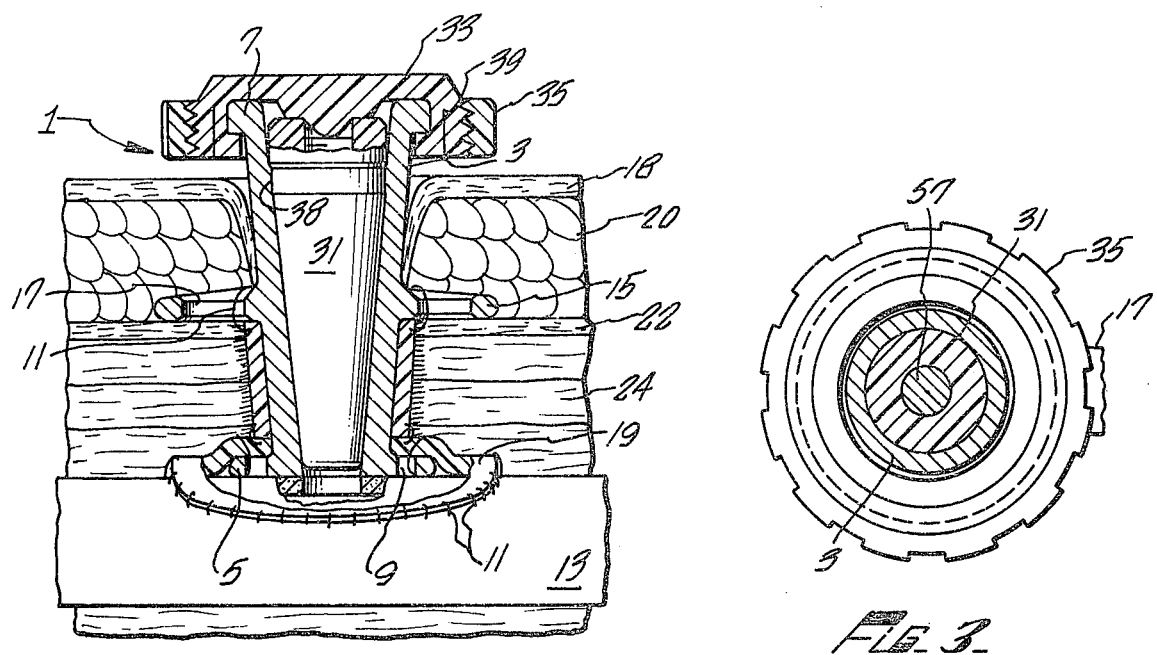
FIG. 1.
FIG. 3.
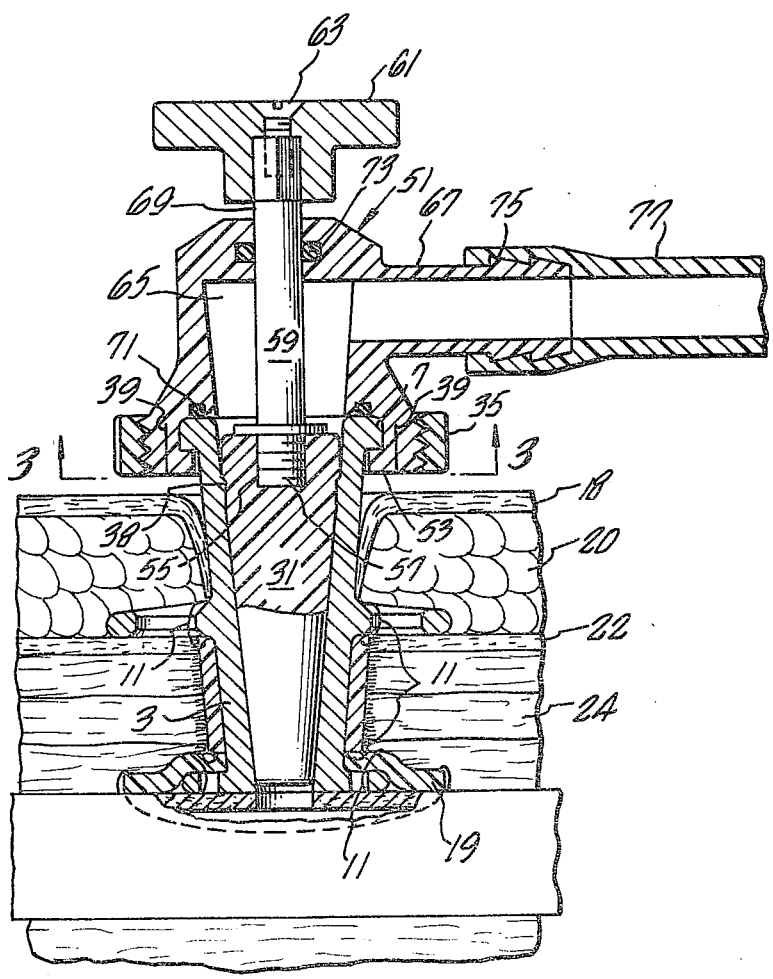
FIG. 2.

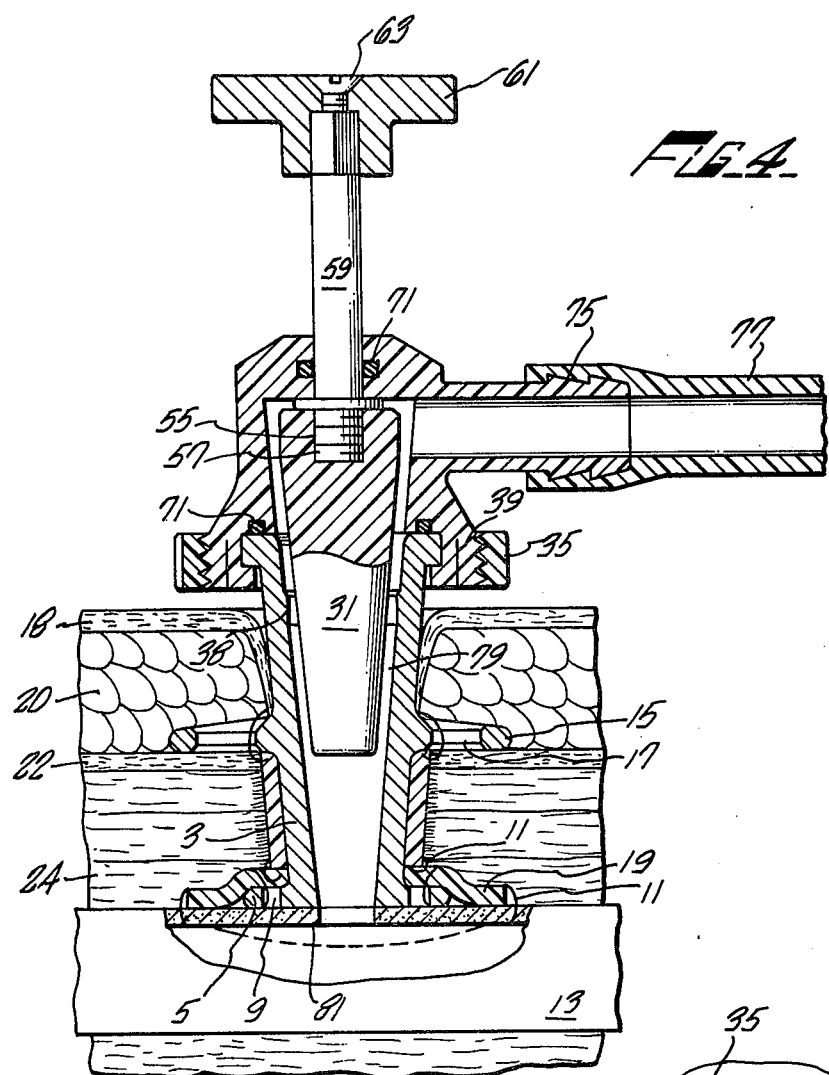
FIG. 4
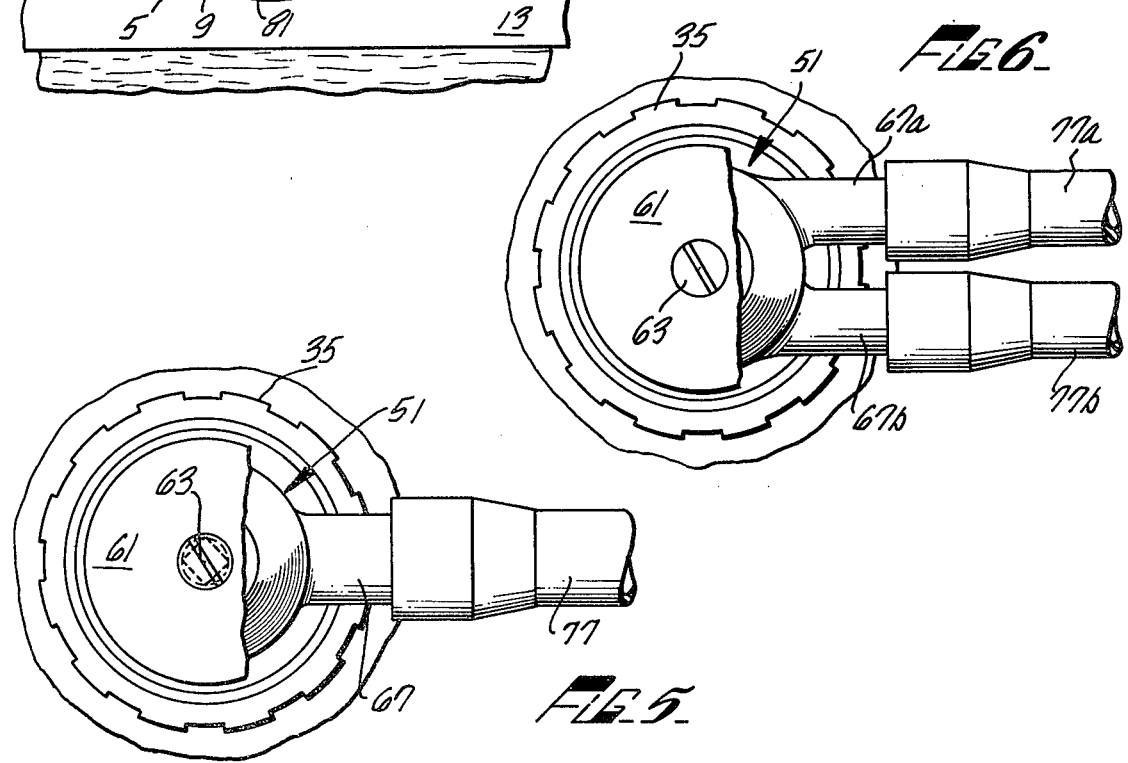
FIG. 6
FIG. 5

ATRAUMATIC BLOOD ACCESS DEVICE VALVE

BACKGROUND OF THE INVENTION

The present invention relates to a blood access device and its method of implantation.

There are a number of situations in which it is necessary to provide for fluid communication with the vascular system. For example, patients suffering from kidney failure require the dialysis of their blood by means external from the body. Blood containing toxic substances, such as urea, uric acid, creatine, phosphorus and calcium, must be removed from the blood system, treated and then returned to the patient. Patients requiring such blood dialysis require treatment at least two or three times per week. Patients suffering from hypoalimentation require a device for providing access to the body's vascular system on at least a daily basis.

One prior method of providing fluid communication with the vascular system involved the insertion of a needle into an artery from which blood to be treated was taken and the insertion of a needle into a patient's vein for blood return. Such a method proved unsatisfactory due to the difficulty in providing for the healing of the artery upon removal of the needle and the trauma produced by the repeated needle insertions. Such shortcomings led to the development of external and, later, internal shunts.

An external shunt involves the insertion of tubes, such as those made of Teflon, into an artery and an adjacent vein in a limb and providing an external communication or shunt between the tubes, which extend from the body of the patient. The shunt between the tubes is required in order to provide flow through the tubes during that period of time that access is not required for blood treatment. Were such circulating blood flow not provided, a blood clot or thrombus could form as would be the case if the tubes were simply capped creating a static blood volume when the tubes were not in use. Dialysis, for example, is accomplished by connecting the arterial and venous tubing to a suitable dialysis unit. However, such a configuration traumatizes the skin adjacent the Teflon tubes and a path is provided through the skin for infection to enter the patient's body. Furthermore, even with external shunts, blood clots sometimes form with the tubes and create a health hazard to the patient.

The disadvantages of external shunts led to the development of the internal shunt. An internal shunt is performed by joining, within a body, openings between an artery and an adjacent vein. The pressure in the artery being substantially greater than that in the vein causes the vein to become distended, forming a fistula. One or two needles were then inserted into the fistula in order to achieve communication with the patient's vascular system. The patient suffers major discomfort and pain each time the needles are inserted into the fistula. Moreover, the continuous intrusion into the fistula causes it to become layered with scar tissue which ultimately prevents further intrusion, thus requiring the formation of another shunt.

Both the internal and external shunts increase the loading on the patient's heart due to the joining of the artery to a vein having a lower pressure, thereby lowering the artery's pressure, and requiring the heart to attempt to regain the original arterial blood pressure. Further, in many cases, the reduced circulation in the distal portion of the limb wherein the shunt is effected impairs the adequate removal of waste products from the muscles and other tissues resulting in weakness of the limb.

An object of the present invention is to provide an atraumatic valve for a blood access device. Other objects and advantages of this invention will become apparent upon a reading of the entire specification, including the drawings and claims.

SUMMARY OF THE INVENTION

The present invention provides for a valve and its method of use in a blood access device which has been permanently implanted through a patient's skin in order to provide access to the patient's vascular system while enabling full circulation throughout the vascular system as no external or internal shunt is required. The device and method of operation may also be utilized for patients which have had an internal shunt operation. After a blood access device has been implanted within a patient's body providing access to a blood vessel of the patient's vascular system, the present invention provides for the atraumatic opening and closing of a valve within the blood access device allowing for blood treatment without trauma to the patient's blood or body tissues surrounding the blood access device.

The valving mechanism of this invention includes a valve chamber which may be connected to that portion of the blood access device blood passageway which is positioned at the body exterior. The valve includes means for gently opening and closing a plugging means positioned within the valve passageway in order to allow for blood flow therethrough. When the plugging means is positioned in its closed configuration, the blood within the blood passageway is substantially expelled into the body's vascular system, therefore minimizing the possibility of infection and the formation of blood clots.

DESCRIPTION OF THE DRAWINGS

FIGS. 1 and 2 are cross-sectional views illustrating the valve device of this invention.

FIG. 3 is a cross-sectional view taken about 3—3 of FIG. 2.

FIGS. 4, 5 and 6 are partial cross-sectional views illustrating the valve device of this invention.

DESCRIPTION OF PREFERRED EMBODIMENTS

Referring now to FIG. 1, the blood access device within which the atraumatic valving mechanism of this invention operates, will be discussed. The blood access device, generally referred to as 1, includes a blood passageway 3 having an external rim or lip 7, an anchor flange 15 and a flange means 5. The flange means 5 is positioned adjacent a blood vessel 13 and secured thereto by means of suitable surgical suture fiber 11 which is also passed through apertures 9 within the flange means 5.

FIG. 1 further illustrates the use of vascular grafting material 19 which both provides for the minimizing of blood loss during implantation surgery and provides structural support for tissue ingrowth which allows the blood vessel 13 and body tissues to be securely anchored to the blood access device 1. FIG. 1 illustrates a patient's skin 18, fat 20, fascia 22 and muscle 24 within which the blood access device 1 is anchored. A plugging means 31 is shown positioned within the blood passageway 3 adapted to prevent blood flow therethrough and to expel blood from the blood passageway 3 upon insertion. The blood passageway is preferably tapered as illustrated in FIG. 1, the taper having an untapered portion along its tapered length as shown as a vertical ring 38 in FIG. 1 in order to provide an improved seal between the plugging means 31 and the blood passageway 3. The plugging means 31 is preferably restrained within the blood passageway 3 by means of a cap means 33 and a thread retaining ring 35 having a number of vertical slits 39 to facilitate the engagement and removal of the retaining ring 35.

The blood access device with which the valve device and method of operation of this invention is utilized is more fully described in pending U.S. Pat. application Ser. No. 813,526, filed on July 7, 1977 and hereby incorporated by reference. Having briefly described the blood access device with which the subject matter of this invention is utilized, the valving mechanism of this invention will now be more fully discussed.

When it is desired to remove blood from a patient's vascular system, restraining ring 35 is unthreaded, thereby allowing cap means 33 to be removed. A connector or valve chamber generally referred to as 51 may be positioned about the external rim or lip 7 of the blood access device 1 and retained in such a position by retaining ring 35. The valve chamber 51 is preferably provided with an engaging lip 53 which mates with ring 7 of the blood access device 1. The valve chamber 51 is also provided with a plurality of slits 39 in order to facilitate its engagement and removal, as was true with respect to cap means 33.

In accordance with this invention, plugging means 31 is provided with an internally threaded aperture 55 adapted to engage the threaded portion 57 of a reciprocal stem member 59. The stem member 59 is rotated, as by means of a wheel assembly 61 suitably secured to the stem member 59 as by means of a screw 63 until the stem member 59 is securely connected to the plugging means 31 by means of engagement of the threaded portion 57 of the stem member 59 with the internally threaded aperture 55 of the plugging means 31. The valve chamber 51 is further provided with a cavity portion 65 adapted to receive at least a portion of the plugging means 31 when said stem member 59 and connected plugging means 31 are pulled from said blood passageway 3 so as to allow blood flow from the blood vessel 13 through the blood passageway 3.

The valve chamber 51 is also provided with a blood outlet 67 and an aperture 69 through which said stem member 59 is allowed to slide or reciprocate as the stem member 59 is pushed or pulled in order to close or open the valve of this invention or rotate it in order to engage or disengage said plugging means 31. Suitable seals 71 and 73, such as O-ring seals, may be employed in order to prevent blood loss during the operation of the valve mechanism of this invention. Suitable retaining means such as annular locking members 75 may be utilized in order to provide for a secure connection between the valve chamber 51 and a tube 77 utilized to transfer blood.

FIG. 3 illustrates a cross-sectional view of the invention showing FIG. 2 taken about lines 3—3. FIG. 4 more clearly illustrates the valving mechanism of the present invention when the valve is in the open position as contrasted with the closed position of FIG. 2. FIGS. 5 and 6 illustrate two embodiments for blood treatment utilizing this device. FIG. 5 illustrates an embodiment wherein blood is alternately removed for treatment and returned to the body through a single tube 77. FIG. 6 illustrates an embodiment wherein two connections to said valve chamber 51 are provided, 67a and 67b, each having corresponding tube connections 77a and 77b. The embodiment as illustrated in FIG. 6 allows for blood removal through one valve chamber connection and blood return through a separate connection. Preferably, the cross-sectional area of the annular opening 79 between plugging means 31 and the blood passageway 3 is at least equal to the cross-sectional area of the blood passageway 3 at the location 81 where the blood passageway 13 is connected to the blood vessel 13.

While the preferred embodiment and the application of this invention have been shown and described, it will be apparent to those skilled in the art that modifications thereto may be made without departing from the inventive concepts herein described. The invention is, therefore, to be limited only by the scope of the claims appended hereto.

What is claimed is:

1. An atraumatic method of valving for a blood passageway of a blood access device, said blood passageway connecting a blood vessel with a body to the body exterior, said blood passageway having a plugging means restrained in a sealing relationship therein preventing flow through said blood passageway, said method comprising:

removing said plugging means restraint;

connecting a valve chamber means to the portion of said blood access device blood passageway at said body exterior, said valve chamber means including a blood outlet and a portion adapted to receive at least a portion of said plugging means;

connecting a reciprocable stem member to said plugging means, said removable stem member passing through said valve chamber means;

pulling said reciprocable stem member and thereby pulling at least a portion of said connected plugging means from said blood passageway into said valve chamber means, and allowing for the passing of blood through said blood passageway and said valve chamber blood outlet;

pushing said reciprocable stem member and thereby pushing said connected plugging means from said valve chamber and into said blood passageway thereby allowing for the expelling of blood from said valve chamber means and said blood passageway and preventing further blood flow therethrough;

disconnecting said stem member from said plugging means;

disconnecting said valving chamber means from said blood access device; and restraining said plugging means within said blood passageway.

2. The atraumatic method of valving for a blood access device claimed in claim 1 wherein said pulling said reciprocable stem member produces an annular aperture about said plugging means having a cross-sectional area at least equal to a cross-sectional area of said blood passageway adjacent its connection to said blood vessel.

3. An atraumatic valving mechanism for operation within a blood passageway of a blood access device, said blood passageway adapted to connect a blood vessel within a body to the body exterior, said valving mechanism comprising:

a plugging means for sealing said blood passageway;
a reciprocable stem member means for connection to said plugging means;
a valve chamber means adapted to be secured to the portion of said blood access device blood passageway at said body exterior, said valve chamber including a blood outlet and an aperture through which said reciprocable stem member means for connection to said plugging means may be passed and;
a retaining ring for securing said valve chamber means to said blood access device, wherein said valve chamber means is further defined as including a plurality of slits, at the portion of said valve chamber means adapted to be secured to the portion of said blood access device, in order to facilitate connection and disconnection of said valve chamber means.

4. The atraumatic valving mechanism claimed in claim 3 wherein
said stem member is further defined as having a threaded portion adapted to be inserted within an internally threaded portion of said plugging means.

5. The atraumatic valving mechanism claimed in claim 3 wherein
said valve chamber further includes a blood inlet.

6. An atraumatic valving mechanicsm for operation within a blood passageway of a blood access device, said blood passageway adapted to connect a blood vessel within a body to the body exterior, said valving mechanism comprising:
a plugging means for sealing said blood passageway;
a reciprocable stem member means for connection to said plugging means;
a valve chamber means adapted to be secured to the portion of said blood access device blood passageway at said body exterior, said valve chamber including a blood outlet and an aperture through which said reciprocable stem member means for connection to said plugging means may be passed, wherein said blood passageway and said plugging means are further defined as having a generally tapered configuration, said blood passageway having a nontapered portion about which said plugging means may be placed and sealed in engaging relationship.

* * * * *